United States Patent [19]

Heimberger

[11] Patent Number: 4,492,098
[45] Date of Patent: Jan. 8, 1985

[54] METHOD OF MAKING A SLIDE FASTENER COUPLING STRIP

[75] Inventor: Helmut Heimberger, Steinhausen, Switzerland

[73] Assignee: Optilon W. Erich Heilmann GmbH, Cham, Switzerland

[21] Appl. No.: 282,075

[22] Filed: Jul. 10, 1981

[30] Foreign Application Priority Data

Jul. 12, 1980 [DE] Fed. Rep. of Germany ....... 3026448

[51] Int. Cl.³ .............................................. D04B 7/16
[52] U.S. Cl. ...................................... 66/202; 66/195; 24/392; 24/393
[58] Field of Search ............................... 66/190–195, 66/202; 24/205.1

[56] References Cited

U.S. PATENT DOCUMENTS 2,228,944  1/1941  Brandt .................................. 66/193
3,864,945  2/1975  Fröhlich .............................. 66/193
3,881,326  5/1975  Bourgeois ........................... 66/203
4,137,733  2/1979  Heimberger ........................ 66/195

FOREIGN PATENT DOCUMENTS

2259790  7/1973  Fed. Rep. of Germany ........ 66/203
1434760  5/1976  United Kingdom ................. 66/195

Primary Examiner—Ronald Feldbaum
Attorney, Agent, or Firm—Karl F. Ross; Herbert Dubno

[57] ABSTRACT

A coupling strip for a slide fastener, which can be utilized as part of a stringer half together with a fabric tape of which it forms a part, or alone as a stringer half, is produced by crocheting at least two rows of knots using bearded (spring-type) or latch needles and respective yarn guides on a crocheting machine, a continuous coupling element in coil or meander form and composed of a synthetic resin monofilament being inserted as a weft across these rows.

1 Claim, 21 Drawing Figures

METHOD OF MAKING A SLIDE FASTENER COUPLING STRIP

FIELD OF THE INVENTION

My present invention relates to a method of making a coupling element strip for a slide fastener and, more particularly, to the fabrication of a unit having a multiplicity of uniformly spaced coupling heads or eyes which are interdigitatable with those of a corresponding strip so that the two strips and any article or tape to which each may be affixed, can form a slide fastener capable of being opened and closed by the movement of a slider therealong.

BACKGROUND OF THE INVENTION

A slide fastener can comprise a pair of stringer halves each of which can have a support tape, e.g. of knitted or woven fabric, along an edge of which a continuous monofilament coupling element can be affixed, this element having a meander or coil pattern or configuration so that it consists of a plurality of coupling members, each of which has a head or eye receivable between a pair of coupling members of the opposing stringer half.

The monofilament strand, which may be composed of a polyamide, thus is formed with a multiplicity of such heads or teeth which can interdigitate with the heads or teeth of the opposing coupling element upon movement of a slider along the slide fastener.

Stringer halves or a continuous band which can be cut into lengths to form such stringer halves can be produced on modified weaving or knitting tape looms with the coupling element inlaid into the product by weft insertion needles or the like with warp pillars in the case of a warp knit fabric, special warp yarns in the case of a woven fabric, or other longitudinal cords serving as binders for retaining the coupling elements on the edge of the fabric tape.

Each coupling member may have, in addition to the head or eye capable of fitting snugly between coupling members of the opposite stringer half, a pair of shanks reaching inwardly to the tape and extending from the coupling head, as well as bights or connecting portions joining each shank with the shank of an adjacent coupling member.

The binding yarns generally run over these shanks or may be interwoven therewith and, in accordance with the principles of slide fastener technology, end stop members can be formed at the ends of each coupling element while a slider can be mounted on a pair of such coupling elements to cause interdigitation of the coupling members upon movement of the slider in one direction and separation of the coupling elements upon movement of the slider in the opposite direction.

It is already known to form a monofilament coupling element of the aforedescribed type as a weft such that the binding strands are looped over the shanks thereof to provide a coupling element strip. Customarily, however, the latter strip is formed by laying in (weft insertion) of the monofilament forming the coupling element during the warp knitting of a tape on a conventional or slightly modified tape knitting loom operating under warp knitting principles.

Generally the knitting operation also forms a tape along the edge of which the coupling element strip is provided.

In practice most conventional processes of this type found commercial acceptability because the formation of warp pillars to engage the monofilament as a weft is comparatively slow on conventional knitting machinery and the engagement of the monofilament may be irregular so that nonuniform products are obtained. The slide fasteners are of insufficient precision and do not have the low dimensional tolerances desired for high quality products.

Experience has shown that in many cases the slide fastener stringers are not adequately resistant to bending stresses in the slide fastener plane so that it is difficult to maintain an exact interhead spacing and thus ensure reliable opening and closing of the slide fastener.

OBJECTS OF THE INVENTION

It is the principal object of the present invention to provide an improved method of making a coupling strip for slide fasteners of a high precision, fixed interhead spacing and low cost at high fabrication speeds.

Another object is to provide an improved coupling strip for a slide fastener which obviates the disadvantages of earlier articles for the same purposes.

SUMMARY OF THE INVENTION

I have found, quite surprisingly, that a coupling strip which can be used directly as a slide fastener half when connected to a garment or other support, or which can form part of a stringer half together with a support tape, can be fabricated rapidly, inexpensively and reliably without the disadvantages which appear to inhere in many processes for producing stringer halves by knitting, when at least two warp knit transversely spaced rows of chain stitches are formed on a crocheting machine by corresponding bearded (spring type) or latch-type needles and respective yarn guides and wherein the monofilament strand adapted to form the coupling element is inserted into each pair of the chain stitches as they are formed by the back-and-forth movement of a weft-insertion guide of the crocheting machine.

Thus each of the rows of stitches is formed continuously from a single yarn by the respective crochet needle and its guide, the loop forming part of a respective knot engaging a shank of the coupling element as it is formed and a meander or coil configuration on the crocheting machine which is provided with respective bearded or spring-type needles for each row and with conventional hole-type guides constrained to move in a coordinated pattern with the respective needles in a crocheting motion (see Die Häkelgalonmaschine, G. Luze Verlag, Saulgau, by R. Buttner, Publ. Eugen Wurt, Germany 1953).

The monofilament thread is thus inserted as a weft inlay into each pair of chain stitches of the two rows as each stitch is formed by the weft yarn guide of the crocheting machine and is thereby knotted tightly to the respective warp row or column. The monofilament yarn and the one or more chain stitches thereby form a fabric-like structure constituting the strip.

The crocheting machine which can be used in accordance with the present invention, deviates from a conventional warp knitting machine in that each yarn forming a respective warp knit or row is fed continuously to the same needle so that each loop also forms a stitch which tightens against and is retained against pulling out, by the shank of the monofilament engaged therein rather than by being retained by the next stitch as is the case with conventional pillars in a warp knit construction. In other words, each stitch of the present invention can engage the shank of a respective coupling member.

Surprisingly, a coupling strip can be formed in accordance with the present invention far more rapidly on a crocheting machine than a corresponding strip on a warp knitting machine and with far greater precision since the interstitch spacing is defined exclusively by the back-and-fourth movement of the weft-inserting guide which forms the coupling element and further, each shank is retained by a respective stitch.

The precision is achieved simultaneously with improved definition of the location of each reversal in direction of the monofilament thread so that each reversal takes place at a precise location whether this reversal is caused by fingers or claws which engage the monofilament before such a reversal or by so-called marabou needles, whether straight or offset, which are introduced into the reversal region to define the location at which each bend should be formed.

The process of the invention is applicable to meander coupling elements as well as to coil coupling elements.

When meander coupling elements are formed, it has been found to be advantageous to pass the monofilament in a planar meander pattern such that at least one row of stitches is provided to each side of the center of the meander and this central region is left free. The assembly is then bent about a longitudinal axis at the center of the meander so that the two opposite sides thereof overlap and the U-shaped bends formed in the meander produce the coupling head mentioned previously.

The U-shaped bending can also position the rows of stitches so that, for example, the row of stitches of one side of the bend lies between the rows of stitches on the opposite side thereof.

The bend also can dispose the row of stitches from one side of the bend adjacent a row of loops on the opposite side thereof or alongside two or more such rows of stitches on the latter side.

Prior to or during the formation of the U-shaped bends, in the region of the bend, the coupling element monofilament can be flattened to provide formations which extend in the direction of the axis of bend to improve the interengagement of each coupling head with the coupling heads of the opposing coupling element.

To hold the shanks of the U-shaped coupling member of a meander coupling element together, tying loops can be slung around these shanks. Thus, the crocheted loops on both sides of the meander center can be tied by a textile weft yarn which, in turn, can form a part of a fabric tape, e.g. which can be knitted or woven and preferably this tying yarn can be composed of a thermally shrinkable material which can then be heated to ensure a tight engagement with the stitches about which this weft is slung.

When the coupling element of the strip is of the coil type, preferably the monofilament thread is inserted as a so-called double weft, i.e. both shanks of each coupling member are engaged in common by the stitches of the two or more knitted rows. In this case, the bend location is retained, two shanks are carried across the rows of stitches and the thread guide and bearded or latch needles form the knit stitches therearound.

Preferably the two shanks are disposed one directly above the other so that they have a common projection in the slide fastener plane. A nonbinding yarn or loop, e.g. forming part of a fabric type, can be received between the two shanks. Naturally, even in this case, the two shanks can be engaged by different stitches after each formation of a coupling eye or head.

In the fabrication of such coiled coupling elements, two coupling strips are preferably formed simultaneously so that the coupling heads of the two strips are formed in interdigitated fashion in a single crocheting machine.

It is also possible to utilize a single machine for the fabrication of a multiplicity of such strips in coupling or disconnected form simultaneously, the number depending, of course, upon the feed of the strips and the width of the machine.

The strips can be formed with tapes directly on the machine as well or can be fed as an edge member to a knitting machine in which weft yarns engage the strip. Furthermore, the tape, when formed simultaneously with the strip and connected thereto, can be produced by a knitting operation utilizing conventional warp knit procedures. It is also possible, however, to simply stitch the strip to a tape or directly to the article to be provided with the slide fastener.

BRIEF DESCRIPTION OF THE DRAWING

The above and other objects, features and advantages of the present invention will become more readily apparent from the following description, reference being made to the accompanying drawing in which.

SPECIFIC DESCRIPTION

FIGS. 1 through 4 show, in sequence, the steps in the formation of the stitches of a crocheting machine utilizing a spring-type needle although it will be understood that a latch-type needle can also be used.

Each row or string of stitches is represented at 1 and is formed continuously from a single yarn 2 utilizing the spring needle 3 which is vertically displaceable in the usual manner while an eye-type guide needle 4 is swingably displaceable as shown.

Figure 1:
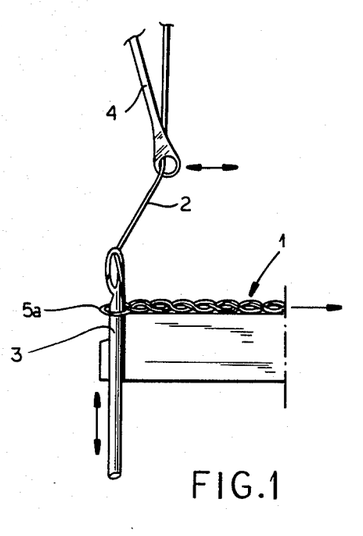
FIGS. 1 through 4 are diagrams illustrating the formation of the stitches on the crocheting machine in accordance with the present invention.
Figure 2:
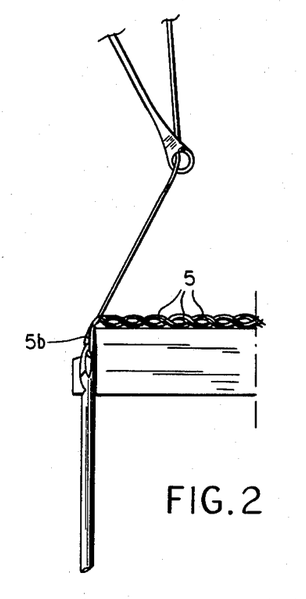
Figure 3:
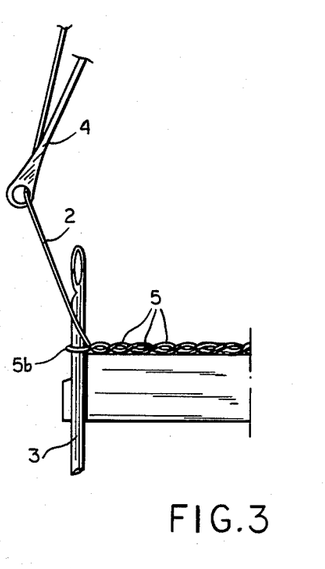
Figure 4:
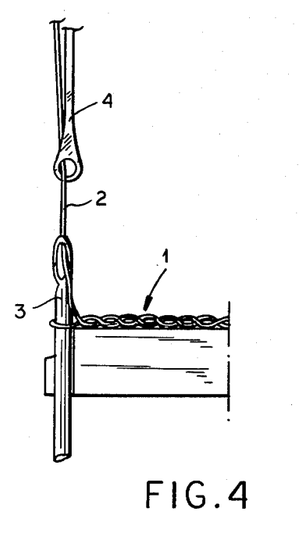

Thus, during the downward stroke of the needle 3 (FIG. 1), while the yarn 2 is held in an extreme right-hand position, the thread is drawn through a previous stitch 5a and forms the next stitch 5b (FIG. 2) whereupon the needle 3 rises in the stitch 5b and, having released the thread, is prepared to grip a portion of the yarn 2 swung in front of and around the needle by the guide 4 (FIG. 3). While the needle 3 is in upper position, the guide 4 swings to the right (FIG. 4) to slip the yarn 2 into the needle eye and the sequence of FIG. 4 is repeated.

According to the invention, as the needle rises preparatorily to forming the next loop, it receives behind it a pass (or two passes) of a synthetic resin monofilament so that the next engagement of the yarn 2 by the needle locks the coupling element strand in place and hence each loop, or every other loop or even every third loop, depending upon the spacing of the coupling heads can engage the coupling element strand. The coupling strip moves off to the right.

Figure 5:
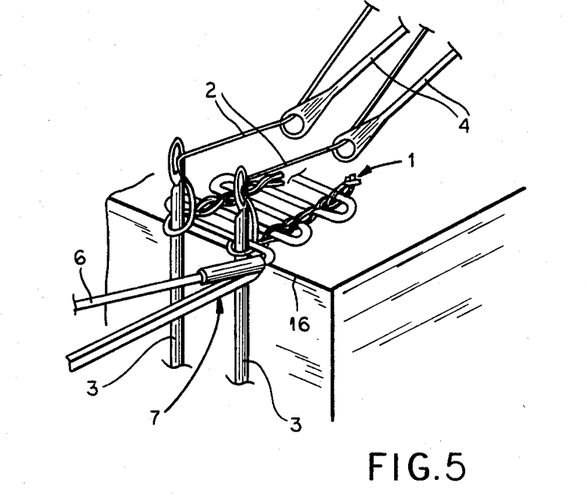
FIGS. 5 and 6 are perspective diagrammatic views illustrating how the knitting action ties in a synthetic resin monofilament in meander configuration as a weft insert.
Figure 6:
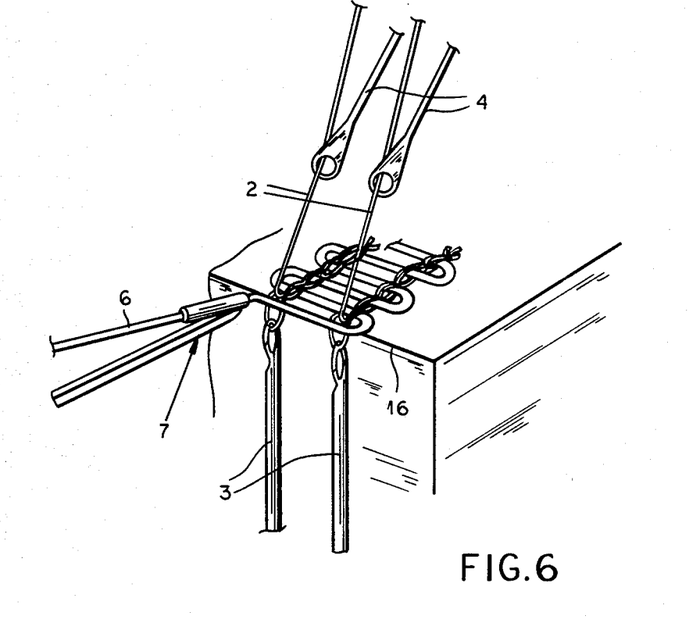

This can be seen as well in FIGS. 5 and 6 in which every other stitch is effective around a length of the coupling element 6.

The coupling element 6 is swept back and forth across the two rows 1 of stitches via a weft insertion guide 7 so that a fabric-like strip is formed.

Figure 7:
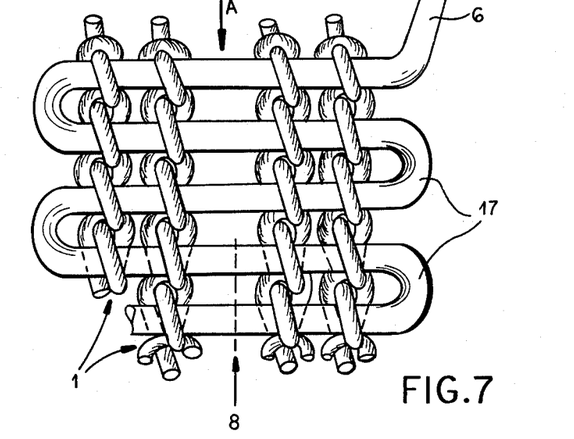
FIG. 7 is a plan view of a portion of a strip in accordance with the present invention prior to bending or folding to form the coupling heads.
Figure 11:
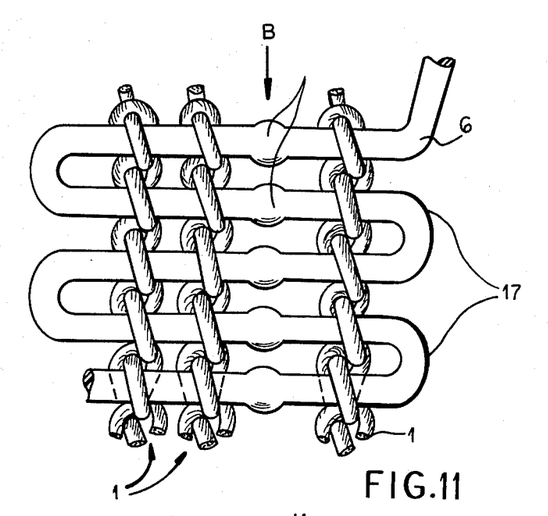
FIG. 11 is a view similar to FIG. 7 illustrating another embodiment of the invention.
Figure 14:
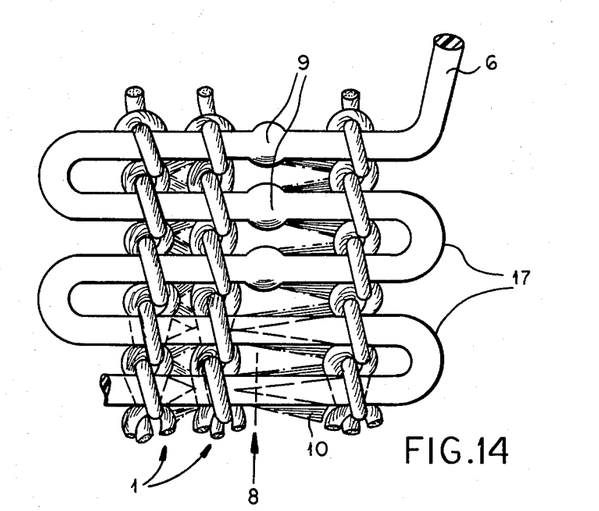
FIGS. 14 through 16 are views corresponding to FIGS. 11 through 13, respectively, showing the formation of a coupling strip with a coil-type coupling element.

As will be apparent from FIGS. 7, 11 and 14, the configurations of these strips may differ.

For example, in the preparation of a strip utilizing a meander, two rows 1 of stitches are formed to each side of a longitudinal median plane represented at 8 and corresponding to the center of the meander.

Figure 8:
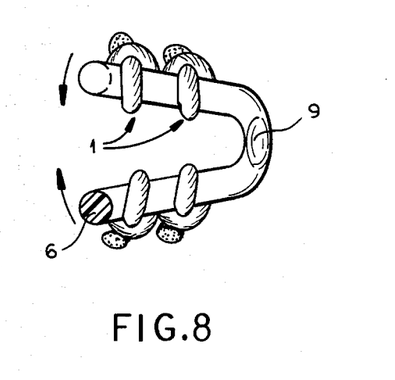
FIGS. 8 and 9 are views corresponding to a view in the direction of the arrow A of FIG. 7 showing the U-shaped bends which are imparted to the strip.
Figure 9:
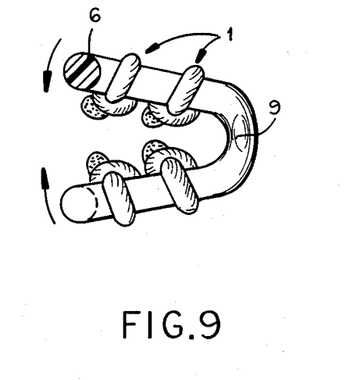

Depending upon the direction in which the meander is bent (see FIGS. 8 and 9) the stitch shanks (FIG. 8) or the stitch knots (FIG. 9) underlying the loops can be brought to bear against one another in imparting a U-shape to the meander.

Figure 10:
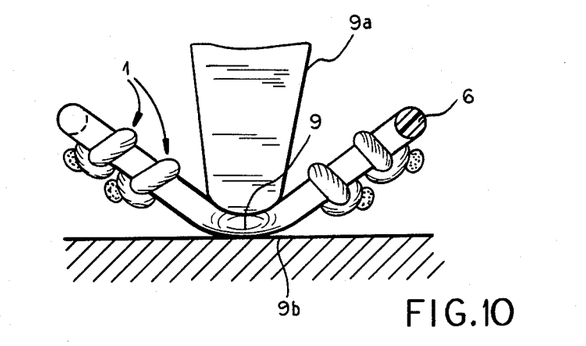
FIG. 10 illustrates the bending process simultaneously with a squeezing of a monofilament to deform and assist in the production of a coupling head.

The bending results in the formation of coupling heads 9 although, as indicated in FIG. 10, the center region of the meander can be deformed (flattened) to enlarge the coupling heads by pressing a tool 9a against the monofilament and urging the monofilament against an anvil 9b.

Figure 12:
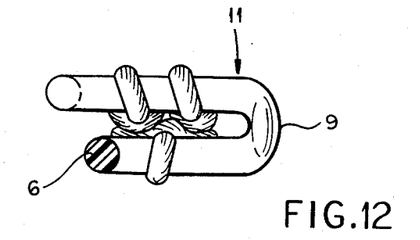
FIG. 12 corresponds to a view in the direction of arrow B but showing the strip after the U-shaped bend.
Figure 13:
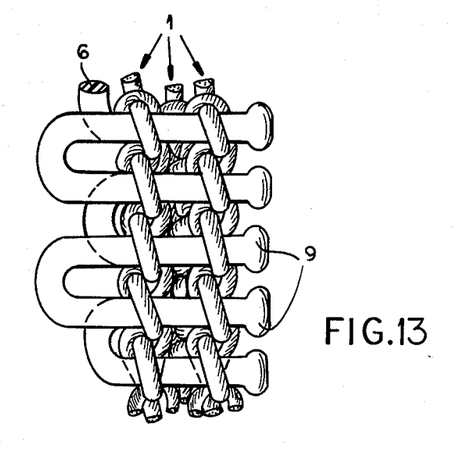
FIG. 13 is a plan view of the strip of FIG. 12.

In FIGS. 11 through 13, the coupling heads 9 can be formed in a similar manner, this embodiment differing from that of FIGS. 6 through 10 by offsetting the row of heads to one side of the meander and providing a single row 1 of stitches to one side and a double row on the opposite side, the spacing of the rows being such that the single row fits between the other two rows (see FIGS. 12 and 13).

Figure 15:
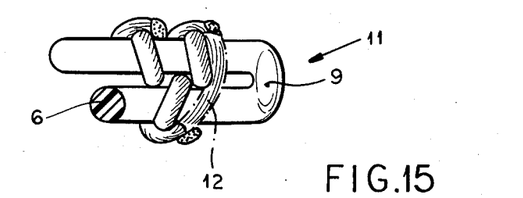
Figure 16:
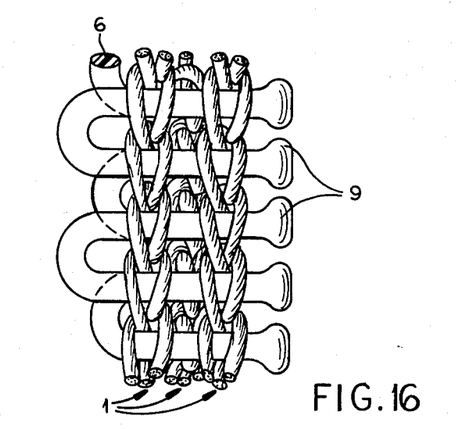

FIGS. 14 through 16 represent an embodiment similar to FIGS. 11 through 13 although here a textile weft insert yarn 10 of shrinkable material is also introduced into the stitches of the warp chains on both sides of the center of the meander. This yarn, upon bending, forms a tie holding the upper and lower stitches together as indicated at 12 in FIG. 15, the tie being tightened by heating and thermal shrinkage.

Figure 17:
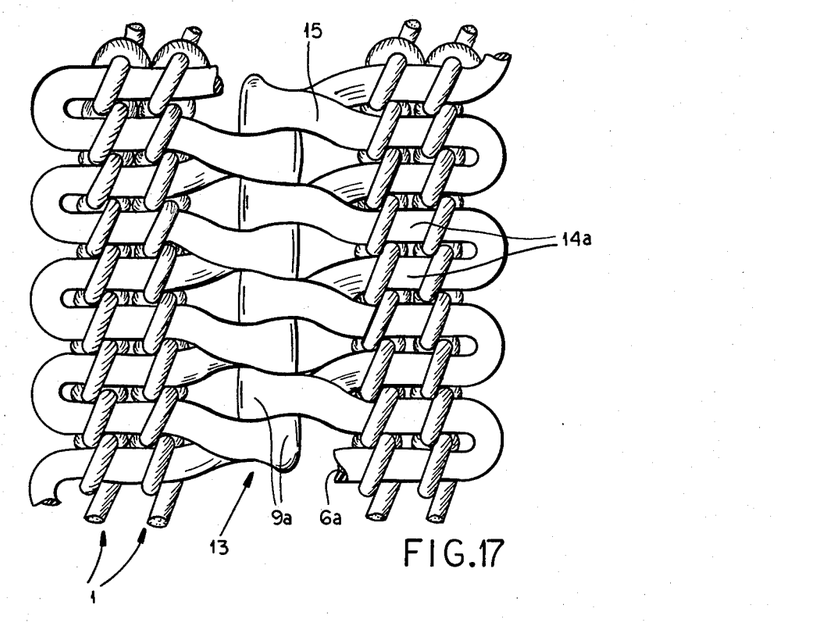
FIG. 17 is a plan view of a strip utilizing a different coil-type coupling element.
Figure 18:
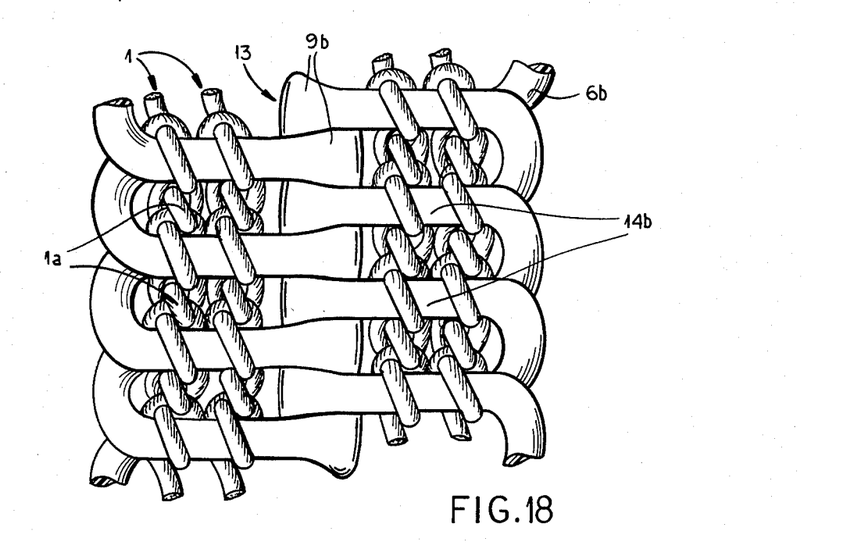
FIG. 18 is a view similar to FIG. 17 showing another embodiment of the invention.

FIGS. 17 and 18 show coupling strips according to the invention with coil-type coupling elements represented at 6a and 6b, respectively, with two strips being formed in interdigitated relation on the same crocheting machine.

In each case, the monofilament forms a double weft insert, i.e. a double pick, in which the bend or direction-change locations are held fixed and form the coupling heads 9a and 9b, respectively.

The shanks 14a in the embodiment of FIG. 17 are engaged individually by the stitches or, as is the case in the embodiment of FIG. 18 and as shown at 14b, in pairs by the loops.

In the embodiment of FIG. 18, moreover, the shanks 14b of a given coupling member lie one above the other and have a common projection on the slide fastener plane.

Between the binding stitches, therefore, there may appear nonbinding stitches 1a.

In the embodiment shown in FIG. 17, the shanks 14a of each coupling member, after passing from the head, are bent toward and eventually brought into a common plane parallel to the plane of the paper as shown at 15.

Figure 19:
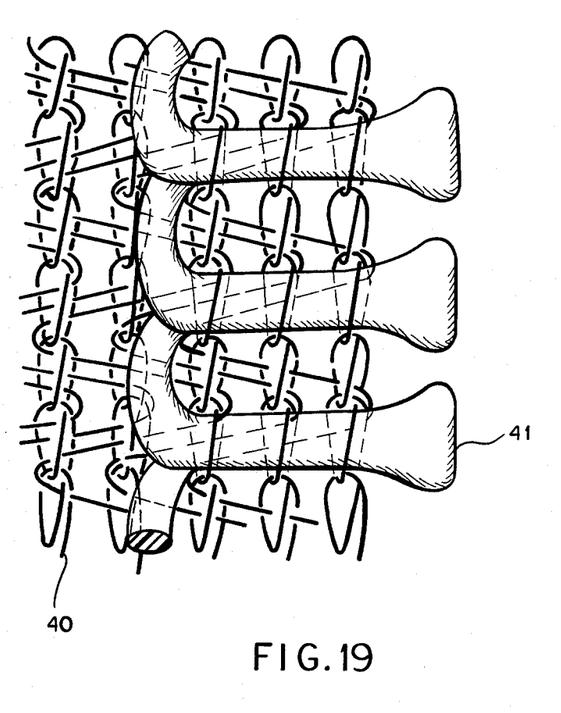
FIGS. 19, 20 and 21 are diagrams illustrating the formation of a knitted slide fastener stringer incorporating a strip of the type shown in FIGS. 17 and 18.
Figure 20:
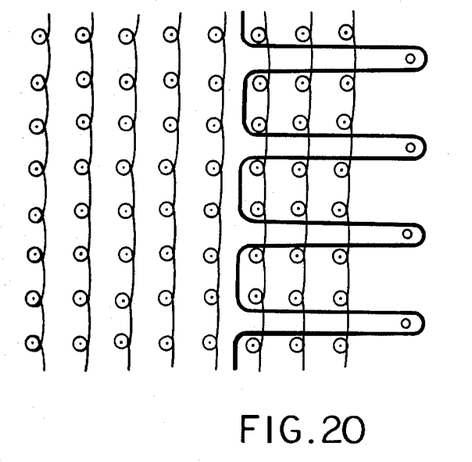
Figure 21:
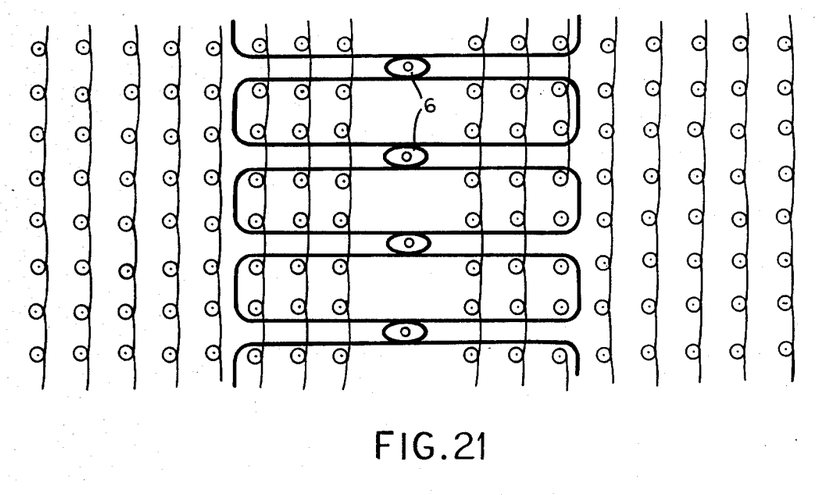

FIGS. 17 and 18 also demonstrate that two strips can be formed simultaneously on the same machine with the bend locations being interfitted so that the coupling elements are interdigitated. In this case, rather than bending the coupling elements simultaneously in a U-configuration, the bend locations can be fixed at the end of each back-and-forth pass of the respective weft-insert thread guide by which the coupling element is deposited. The stitch rows 1 can engage the weft inserts of knitted rows formed as illustrated in FIG. 19 and utilizing the patterns shown in FIGS. 20 and 21, if desired, to simultaneously form tapes as represented at 40 in FIG. 19 from which the heads 41 of the coupling members project. FIG. 20 shows the formation of a single stringer half whereas FIG. 21 represents the formation of a pair of stringer halves for interdigitated coupling elements.

In the embodiment of FIG. 18, for each stitch formation, a double weft insert for a coupling element is required because both coupling member shanks must form the double-weft insert. Consequently, the weft insert guide must be given a back-and-forth motion when the needles are drawn into the so-called knocking over comb. Both strokes of the guide can be utilized to advantage in the formation of stitches for engagement with or the formation of a tape. The latter can be utilized as in weft plush fabrication to establish a precise turning point between a forward and return stroke, utilizing marabou-like needles or other devices.

Other straight or offset needles can be utilized to engage the monofilament strand in the formation of the coupling heads to hold them in position during the return stroke of the guide.

When claws or the like are utilized, to form the coupling heads when the bights 17 are formed by the bearded or latch needles, the claw can be provided with a stripper to release each head as it is formed.

It is also possible to provide a core wire about which the heads are formed and to mount the core wire on a holder so that the eyes slide along this holder until they are fixed whereafter they can be withdrawn from the core wire. The positioning of the core wire can be effected by mechanical or electrical means.

The alternate insertion of the coupling element threaded in the form of two interconnected strips can be avoided if the bearded or latch needles for the individual strips are partly offset toward one another. This can be achieved without difficulty and in a crocheting machine for the fabrication of high precision strips.

The embodiments of FIGS. 17 and 18, which are of major importance, are characterized by closed fringe or pillar structures forming the stitch rows both in the region in which the strip can be attached by stitching to a tape or another article and in the region of the rows close to the heads. At least two rows of each strip thus can form binding rows for accurately positioning the heads and further, these rows can engage the tape-forming yarns.

I claim:

1. A method of making a coupling strip for a slide fastener stringer comprising the steps of:

knitting a pair of relatively closely spaced warp chains and a further warp chain spaced from the pair of warp chains of a distance greater than the distance between the warp chains of said pair by sweeping respective thread guides for a warp filament for each chain back and forth with respect to a stitch-forming needle and inserting the synthetic resin monofilament thread into the stitches of said warp chain as they are formed to generate a fabric with said synthetic resin monofilament thread forming a weft inlay;

connecting the stitches of said warp chains by a weft-inserted thermally shrinkable yarn;

bending said fabric along a zone between said pair of warp chains and said further warp chain to form respective bends in said synthetic resin monofilament thread such that such bends from slide fastener coupling heads, while said further warp chain is disposed between the warp chains of said pair; and thereafter subjecting the bent fabric to heat to shrink said thermally shrinkable yarn and lock said further warp chain between the warp chains of said pair.

* * * * *